United States Patent
Norton et al.

(10) Patent No.: US 10,275,570 B2
(45) Date of Patent: Apr. 30, 2019

(54) CLOSED LOOP ALERT MANAGEMENT

(71) Applicant: CERNER INNOVATION, INC., Kansas City, KS (US)

(72) Inventors: Joel Robert Norton, Overland Park, KS (US); Christopher Dillard Cline, Smithville, MO (US); Steven E. Harlow, Lee's Summit, MO (US); Scott Gordon Siebers, Leawood, KS (US); Damon Matthew Herbst, Shawnee, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 247 days.

(21) Appl. No.: 15/290,443

(22) Filed: Oct. 11, 2016

(65) Prior Publication Data

US 2017/0032093 A1 Feb. 2, 2017

Related U.S. Application Data

(63) Continuation-in-part of application No. 14/877,808, filed on Oct. 7, 2015, now Pat. No. 9,582,978, which
(Continued)

(51) Int. Cl.
*G06F 19/00* (2018.01)
*H04M 1/725* (2006.01)
(Continued)

(52) U.S. Cl.
CPC ......... *G06F 19/3418* (2013.01); *G16H 10/60* (2018.01); *G16H 40/20* (2018.01);
(Continued)

(58) Field of Classification Search
CPC combination set(s) only.
See application file for complete search history.

(56) References Cited

U.S. PATENT DOCUMENTS

| 4,237,344 A | 12/1980 | Moore |
| 5,319,355 A | 6/1994 | Russek |

(Continued)

OTHER PUBLICATIONS

"Extension Mobile for Enterprise Healthcare Organizations Now Available on Apple iPhone and iPod Touch Via Apple AppStore," http://www.extensionhealthcare.com, Extension, Inc., Fort Wayne, IN, Jan. 10, 2011, 2 pages.
(Continued)

*Primary Examiner* — Travis R Hunnings
(74) *Attorney, Agent, or Firm* — Shook, Hardy & Bacon L.L.P.

(57) ABSTRACT

Methods, computer systems, and computer-storage medium are provided for providing closed loop alert management. An alert related to a patient is communicated to a first tier via a messaging application. The first tier comprises one or more clinicians assigned to care for the patient. Upon receiving a response from a clinician in the first tier, an indication the clinician has responded to the alert is communicated to the first tier. Upon receiving no response from a clinician in the first tier, the alert may be communicated to other devices associated with the clinicians in the first tier or to a subsequent tier comprising one or more other clinicians.

19 Claims, 7 Drawing Sheets

Related U.S. Application Data is a continuation of application No. 13/731,191, filed on Dec. 31, 2012, now Pat. No. 9,185,202.

(51) Int. Cl.
| | |
|---|---|
| *H04M 19/04* | (2006.01) |
| *G16H 80/00* | (2018.01) |
| *G16H 10/60* | (2018.01) |
| *G16H 40/20* | (2018.01) |
| *G08B 25/01* | (2006.01) |
| *G08B 27/00* | (2006.01) |

(52) U.S. Cl.
CPC ........ *G16H 80/00* (2018.01); *H04M 1/72541* (2013.01); *H04M 19/04* (2013.01); *G08B 25/016* (2013.01); *G08B 27/006* (2013.01)

(56) References Cited

U.S. PATENT DOCUMENTS

| | | | |
|---|---|---|---|
| 5,319,363 A | 6/1994 | Welch et al. |
| 5,534,851 A | 7/1996 | Russek |
| 5,942,986 A | 8/1999 | Shabot et al. |
| 5,999,846 A | 12/1999 | Pardey et al. |
| 6,754,516 B2 | 6/2004 | Mannheimer |
| 6,804,656 B1 | 10/2004 | Rosenfeld et al. |
| 6,928,370 B2 | 8/2005 | Anuzis et al. |
| 7,035,622 B2 | 4/2006 | Pappalardo et al. |
| 7,035,623 B2 | 4/2006 | Pappalardo et al. |
| 7,090,053 B2 | 8/2006 | Bothwell et al. |
| 7,123,950 B2 | 10/2006 | Mannheimer |
| 7,215,945 B2 | 5/2007 | Pappalardo et al. |
| 7,224,281 B2 | 5/2007 | Santoso et al. |
| 7,225,408 B2 | 5/2007 | O'Rourke |
| 7,249,036 B2 | 7/2007 | Bayne |
| 7,256,708 B2 | 8/2007 | Rosenfeld et al. |
| 7,307,543 B2 | 12/2007 | Rosenfeld et al. |
| 7,315,825 B2 | 1/2008 | Rosenfeld et al. |
| 7,321,862 B2 | 1/2008 | Rosenfeld et al. |
| 7,430,692 B2 | 9/2008 | White, III et al. |
| 7,454,359 B2 | 11/2008 | Rosenfeld et al. |
| 7,475,019 B2 | 1/2009 | Rosenfeld et al. |
| D599,812 S | 9/2009 | Hirsch |
| D599,813 S | 9/2009 | Hirsch |
| D607,004 S | 12/2009 | Kordus et al. |
| D625,317 S | 10/2010 | Jewitt et al. |
| D631,891 S | 2/2011 | Vance et al. |
| D640,276 S | 6/2011 | Woo |
| 7,981,032 B2 | 7/2011 | Santoso et al. |
| 8,015,030 B2 | 9/2011 | Brown |
| 8,092,380 B2 | 1/2012 | Rothman et al. |
| 8,100,829 B2 | 1/2012 | Rothman et al. |
| 8,122,006 B2 | 2/2012 | de Castro Alves et al. |
| 8,160,895 B2 | 4/2012 | Schmitt et al. |
| 8,165,893 B1 | 4/2012 | Goldberg et al. |
| 8,170,887 B2 | 5/2012 | Rosenfeld et al. |
| 8,175,895 B2 | 5/2012 | Rosenfeld et al. |
| D662,507 S | 6/2012 | Mori et al. |
| D665,399 S | 8/2012 | Carpenter et al. |
| 8,332,017 B2 | 12/2012 | Tarassenko et al. |
| 8,355,925 B2 | 1/2013 | Rothman et al. |
| 8,374,988 B2 | 2/2013 | Gawlick |
| 8,401,606 B2 | 3/2013 | Mannheimer |
| 8,401,607 B2 | 3/2013 | Mannheimer |
| 8,403,847 B2 | 3/2013 | Rothman et al. |
| 8,416,085 B2 | 4/2013 | Gawlick |
| 8,417,233 B2 | 4/2013 | Woloshyn |
| 8,417,662 B2 | 4/2013 | Gawlick |
| D682,294 S | 5/2013 | Kanalakis, Jr. et al. |
| D682,844 S | 5/2013 | Friedlander et al. |
| D682,858 S | 5/2013 | Frijlink |
| 8,451,101 B2 | 5/2013 | Somasundaram et al. |
| 8,454,506 B2 | 6/2013 | Rothman et al. |
| D686,221 S | 7/2013 | Brinda et al. |
| 8,543,534 B2 | 9/2013 | Alves et al. |
| D695,773 S | 12/2013 | Tagliabue et al. |
| D696,682 S | 12/2013 | Kim et al. |
| 8,615,291 B2 | 12/2013 | Moorman et al. |
| D700,914 S | 3/2014 | Jin et al. |
| D701,221 S | 3/2014 | Ahmed et al. |
| D705,239 S | 5/2014 | Thompson et al. |
| 8,775,196 B2 | 7/2014 | Simpson et al. |
| 8,838,196 B2 | 9/2014 | Mannheimer |
| 8,842,001 B2 | 9/2014 | Gilham et al. |
| D714,817 S | 10/2014 | Lee |
| D715,820 S | 10/2014 | Rebstck |
| D717,808 S | 11/2014 | Tsuru et al. |
| 8,886,663 B2 | 11/2014 | Gainsboro et al. |
| 8,886,792 B2 | 11/2014 | Biondi et al. |
| D719,577 S | 12/2014 | Tsuru et al. |
| D720,766 S | 1/2015 | Mandal et al. |
| 8,948,734 B2 | 2/2015 | Vaglio et al. |
| D733,175 S | 6/2015 | Bae |
| 9,052,809 B2 | 6/2015 | Vesto |
| D734,349 S | 7/2015 | Amin et al. |
| D734,350 S | 7/2015 | Inose et al. |
| D736,789 S | 8/2015 | Tursi et al. |
| 9,159,313 B2 | 10/2015 | Saeki et al. |
| D742,909 S | 11/2015 | Lee et al. |
| 9,185,202 B2 * | 11/2015 | Herbst ................. G08B 25/016 |
| D747,343 S | 1/2016 | Brinda et al. |
| D751,097 S | 3/2016 | Sarafa et al. |
| D752,604 S | 3/2016 | Zhang |
| D752,614 S | 3/2016 | Kwon et al. |
| 9,280,637 B2 | 3/2016 | Vaglio et al. |
| D753,165 S | 4/2016 | Watson |
| D753,707 S | 4/2016 | Yang |
| D754,176 S | 4/2016 | Kim |
| D757,771 S | 5/2016 | Drozd et al. |
| D757,778 S | 5/2016 | Lemay |
| D758,386 S | 6/2016 | Zhang |
| D758,400 S | 6/2016 | Chang et al. |
| D759,687 S | 6/2016 | Chang et al. |
| D760,738 S | 7/2016 | Scalisi et al. |
| 9,400,874 B2 | 7/2016 | Powell et al. |
| D762,676 S | 8/2016 | Lim |
| D763,290 S | 8/2016 | Gupta et al. |
| D763,881 S | 8/2016 | Smith et al. |
| D763,882 S | 8/2016 | Liang |
| D764,511 S | 8/2016 | Han et al. |
| D765,110 S | 8/2016 | Liang |
| D766,294 S | 9/2016 | Smith |
| D767,605 S | 9/2016 | Mensinger et al. |
| 9,449,355 B2 | 9/2016 | Kozicki et al. |
| D770,491 S | 11/2016 | Jung |
| D771,667 S | 11/2016 | Woo |
| D771,670 S | 11/2016 | Chan et al. |
| D772,259 S | 11/2016 | Pahwa et al. |
| D775,167 S | 12/2016 | Vazquez |
| D777,184 S | 1/2017 | Yang et al. |
| D777,758 S | 1/2017 | Kisselev et al. |
| D778,929 S | 2/2017 | Mensinger et al. |
| D779,517 S | 2/2017 | Pierson et al. |
| D780,191 S | 2/2017 | Kelley |
| 9,582,978 B2 | 2/2017 | Herbst et al. |
| D781,315 S | 3/2017 | Wang |
| D784,384 S | 4/2017 | Hong et al. |
| D785,003 S | 4/2017 | Yun et al. |
| D785,008 S | 4/2017 | Lim et al. |
| D785,009 S | 4/2017 | Lim et al. |
| D785,012 S | 4/2017 | Jou |
| D785,029 S | 4/2017 | Gedrich et al. |
| 9,626,479 B2 | 4/2017 | Zaleski |
| 9,659,482 B2 | 5/2017 | Yang et al. |
| D789,947 S | 6/2017 | Sun |
| D789,949 S | 6/2017 | Sun |
| 9,706,966 B2 | 7/2017 | Colman et al. |
| 9,747,778 B2 | 8/2017 | Mukherji et al. |
| 9,805,573 B2 | 10/2017 | Herbst et al. |
| 9,836,940 B2 | 12/2017 | Herbst et al. |
| 9,881,475 B2 | 1/2018 | Herbst et al. |
| 9,911,300 B2 | 3/2018 | Herbst et al. |
| 9,924,908 B2 | 3/2018 | Hubert et al. |
| 2002/0040282 A1 | 4/2002 | Bailey et al. |

(56) References Cited

U.S. PATENT DOCUMENTS

| | | | |
|---|---|---|---|
| 2003/0163789 A1 | 8/2003 | Blomquist | |
| 2003/0191730 A1 | 10/2003 | Adkins et al. | |
| 2004/0073453 A1 | 4/2004 | Nenov et al. | |
| 2005/0065817 A1* | 3/2005 | Mihai | A61B 5/0002 705/2 |
| 2005/0146431 A1 | 7/2005 | Hastings et al. | |
| 2005/0151640 A1 | 7/2005 | Hastings | |
| 2006/0049936 A1 | 3/2006 | Collins et al. | |
| 2006/0161457 A1 | 7/2006 | Rapaport et al. | |
| 2007/0239488 A1 | 10/2007 | DeRosso | |
| 2008/0021709 A1 | 1/2008 | Greer | |
| 2008/0074951 A1 | 3/2008 | Hubicki | |
| 2009/0048868 A1 | 2/2009 | Portnoy et al. | |
| 2010/0001838 A1 | 1/2010 | Miodownik et al. | |
| 2010/0123587 A1 | 5/2010 | Walls | |
| 2010/0137693 A1 | 6/2010 | Porras et al. | |
| 2010/0223071 A1 | 9/2010 | Kland et al. | |
| 2011/0001605 A1* | 1/2011 | Kiani | G06F 19/3418 340/5.6 |
| 2011/0054946 A1 | 3/2011 | Coulter et al. | |
| 2011/0106560 A1* | 5/2011 | Eaton, Jr. | G01C 21/20 705/3 |
| 2011/0196306 A1 | 8/2011 | De La Huerga | |
| 2011/0208816 A1 | 8/2011 | Chavez | |
| 2011/0295621 A1 | 12/2011 | Farooq et al. | |
| 2012/0075103 A1 | 3/2012 | Powell et al. | |
| 2012/0101847 A1 | 4/2012 | Johnson et al. | |
| 2012/0169467 A1 | 7/2012 | Condra | |
| 2012/0278104 A1 | 11/2012 | Traughber et al. | |
| 2012/0284040 A1 | 11/2012 | Dupin | |
| 2013/0009783 A1 | 1/2013 | Tran | |
| 2013/0049950 A1* | 2/2013 | Wohlert | H04M 11/04 340/531 |
| 2013/0065569 A1 | 3/2013 | Leipzig et al. | |
| 2013/0085765 A1 | 4/2013 | Tuchinda et al. | |
| 2013/0085798 A1 | 4/2013 | Spatola et al. | |
| 2013/0096953 A1* | 4/2013 | Beverly | G06F 19/3418 705/3 |
| 2013/0103768 A1 | 4/2013 | Freebeck | |
| 2013/0104077 A1 | 4/2013 | Felt | |
| 2013/0162424 A1 | 6/2013 | Treacy | |
| 2013/0183923 A1 | 7/2013 | Brackett et al. | |
| 2013/0297348 A1 | 11/2013 | Cardoza et al. | |
| 2014/0039351 A1 | 2/2014 | Mix et al. | |
| 2014/0051399 A1 | 2/2014 | Walker et al. | |
| 2014/0070939 A1 | 3/2014 | Halverson et al. | |
| 2014/0085080 A1 | 3/2014 | Carnes | |
| 2014/0097961 A1 | 4/2014 | Vaglio et al. | |
| 2014/0099929 A1 | 4/2014 | Vaglio et al. | |
| 2014/0100873 A1 | 4/2014 | Vaglio et al. | |
| 2014/0132413 A1 | 5/2014 | Fox et al. | |
| 2014/0172996 A1 | 6/2014 | Deeter et al. | |
| 2014/0184408 A1 | 7/2014 | Herbst et al. | |
| 2014/0358585 A1 | 12/2014 | Reiner | |
| 2015/0081339 A1 | 3/2015 | Vaglio et al. | |
| 2015/0137968 A1 | 5/2015 | Rusin et al. | |
| 2015/0148617 A1 | 5/2015 | Friedman | |
| 2015/0254957 A1 | 9/2015 | Wilson et al. | |
| 2016/0027277 A1 | 1/2016 | Herbst et al. | |
| 2016/0110040 A1 | 4/2016 | Vaglio et al. | |
| 2016/0360160 A1 | 12/2016 | Eizenberg | |
| 2017/0024091 A1 | 1/2017 | Hosier, Jr. | |
| 2017/0098037 A1 | 4/2017 | Agassi et al. | |
| 2017/0109018 A1 | 4/2017 | Vaglio et al. | |
| 2017/0193801 A1 | 7/2017 | Bala et al. | |
| 2017/0265819 A1 | 9/2017 | Colma et al. | |
| 2018/0110477 A1 | 4/2018 | Collins, Jr. et al. | |
| 2018/0153455 A1 | 6/2018 | Guazzi et al. | |

OTHER PUBLICATIONS

"Extension, Inc. and AeroScout Partner to Deliver Solutions for Healthcare RTLS and VoIP," http://www.extensionhealthcare.com, Extension, Inc., Fort Wayne, IN, Feb. 19, 2010, 2 pages.

"Extension, Inc. Launches New Interactive Communications Solution," http://www.extensionhealthcare.com, Extension, Inc., Fort Wayne, IN, May 25, 2011, 3 pages.

"The American Hospital Association Endorses the Extension Healthid smart card system," http://www.news-medical.net, Published Aug. 21, 2009, 2 pages.

First Action Interview Preinterview Communication dated Dec. 4, 2014 in U.S. Appl. No. 13/731,191 5 pages.

First Action Interview Office Action dated Jun. 3, 2015 in U.S. Appl. No. 13/731,191, 4 pages.

Non-Final Office Action dated Jan. 30, 2014 in U.S. Appl. No. 13/711,217, 8 pages.

Final Office Action dated Jun. 19, 2014 in U.S. Appl. No. 13/711,217, 8 pages.

Final Office Action dated Jul. 7, 2014 in U.S. Appl. No. 13/711,177, 12 pages.

First Action Interview Pre-Interview Communication dated Sep. 25, 2014 in U.S. Appl. No. 13/711,206, 5 pages.

Notice of Allowance dated Sep. 29, 2014 in U.S. Appl. No. 13/711,217, 7 pages.

Final Office Action dated Feb. 20, 2015 in U.S. Appl. No. 13/711,177, 11 pages.

Non-Final Office Action dated Mar. 17, 2015 in U.S. Appl. No. 13/711,206, 8 pages.

Non-Final Office Action dated Jul. 8, 2015 in U.S. Appl. No. 13/711,177, 5 pages.

Final Office Action dated Oct. 2, 2015 in U.S. Appl. No. 13/711,206, 15 pages.

Notice of Allowance dated Oct. 29, 2015 in U.S. Appl. No. 13/711,177, 9 pages.

Non-Final Office Action dated Feb. 25, 2016 in U.S. Appl. No. 13/711,206, 17 pages.

Final Office Action dated Nov. 3, 2016 in U.S. Appl. No. 13/711,206, 20 pages.

Non-Final Office Action dated Mar. 23, 2017 in U.S. Appl. No. 13/711,206, 10 pages.

First Action Interview Preinterview Communication dated Apr. 13, 2017 in U.S. Appl. No. 14/551,555, 5 pages.

First Action Interview Pre-Interview Communication dated Jun. 30, 2017 in U.S. Appl. No. 15/131,231, 5 pages.

Non-Final Office Action dated Jul. 13, 2017 in U.S. Appl. No. 29/602,910, 14 pages.

Notice of Allowance dated Jul. 19, 2017 in U.S. Appl. No. 29/602,800, 15 pages.

Final Office Action dated Jul. 27, 2017 in U.S. Appl. No. 13/711,206, 14 pages.

First Action Interview Office Action dated Aug. 9, 2017 in U.S. Appl. No. 14/551,555, 8 pages.

Notice of Allowance dated Dec. 19, 2017 in U.S. Appl. No. 15/684,565, 9 pages.

Notice of Allowance dated Jan. 10, 2018 in U.S. Appl. No. 15/684,563, 5 pages.

Final Office Action dated Jan. 23, 2018 in U.S. Appl. No. 14/551,555, 22 pages.

Notice of Allowance dated Jan. 30, 2018 in U.S. Appl. No. 15/131,231, 7 pages.

Final Office Action dated Mar. 2, 2018 in U.S Appl. No. 29/602,910, 13 pages.

Non-Final Office Action dated Apr. 24, 2018 in U.S. Appl. No. 14/875,800, 22 pages.

Notice of Allowance dated Apr. 25, 2018 in U.S. Appl. No. 15/131,231, 5 pages.

How to create a cool and usable CSS3 search box, dated Feb. 18, 2011, catalin.red [online], [retrieved Feb. 23, 2018]. Retrieved from internet <URL:https://catalin.red/how-to-create-a-cool-and-usable-css3-search-box/> (Year: 2011).

How to Add Search Bar in Table View, by Simon NG, dated Jul. 8, 2012, appcoda.com [online], [retrieved Feb. 23, 2018]. Retrieved from internet <URL:https://www.appcoda.com/how-to-add-search-bar-uitableview/> (Year: 2012).

Riano et al., "MPM: A Knowledge-based functional model of medical practice", Journal of Biomedical Informatics 46 (2013) 379-387.

(56) References Cited

OTHER PUBLICATIONS

Preinterview First Office Action dated Aug. 17, 2017 in U.S. Appl. No. 15/392,926, 4 pages.
Non-Final Office Action dated Sep. 21, 2017 in U.S. Appl. No. 15/630,617, 7 pages.
Notice of Allowance dated Sep. 28, 2017 in U.S. Appl. No. 15/392,926, 7 pages.
Notice of Allowance dated Oct. 30, 2017 in U.S. Appl. No. 15/630,617, 7 pages.
Preinterview First Office Action dated Nov. 15, 2017 in U.S. Appl. No. 15/684,565, 5 pages.
"Clinical Workflow Solutions Extension HealthAlert" brochure published by NEC Corporation Sep. 17, 2012.
Press Release by Extension Healthcare entitled: "Arc Solutions and Extension, Inc. Announce New Collaboration Software Solutions, Specifically Designed for the Healthcare Sector", Jan. 7, 2010.
Notice of Allowance dated Jan. 5, 2017 in U.S. Appl. No. 14/877,808, 5 pages.
How to download Skype app on Android and do Voice and video chat, Oct. 29, 2012, 5 pages. Available at: http://www.howto-connect.com/how-to-download-skype-app-on-android-and-do-voice-and-video-chat/.
Find and replace pop-up window, by Jerome Detraz, dated Jul. 17, 2013, sketchappsource.com [online], [retrieved Jul. 9, 2017]. Available from internet <URL: https://web.archive.org/web/2130717090053/https://www.sketchappsources.com/free-source/190-find-replace-pop-up-window.html.
Preinterview First Office Action dated Nov. 30, 2017 in U.S. Appl. No. 15/684,563, 5 pages.
How to Set Up Zoom on Android, http://blog.recovery-android.com/set-up-zoom-in-android/, Jan. 14, 2016, 3 pages.
ExDialer Dialer & Contacts, Modoohut Communication, Android Apps on Google Play Accessed Apr. 24, 2017 at: https://play.google.com/store/apps/details?id=com.modoohut.dialer&hl=en, 3 pages.
"Contactive—A Caller ID App that Showcases Android's Openess, 3 pages. Accessed Apr. 24, 2017 at: http://techdomino.com/contactive-a-caller-id-app-that-showcases-androids-openess/".
"Review: Our Favourite Effective Contact Managers, Contaker Blog, 6 pages. Accessed Apr. 24, 2017 at: http://blog.contaker.com/?p=61".
How to Design an iPhone App in Photoshop, by Tony Thomas, dated Oct. 26, 2011, medialoot.com [online], [retrieved Jul. 3, 2017], Available from internet URL: https://medialoot.com/blog/how-to-design-an-iphone-app-in-photoshop/.
First Action Interview Pre-Interview Communication dated Jul. 6, 2018 in U.S. Appl. No. 14/983,685, 9 pages.
Non-Final Office Action dated Jul. 25, 2018 in U.S. Appl. No. 15/837,856, 7 pages.
Non-Final Office Action dated Jul. 26, 2018 in U.S. Appl. No. 15/873,158, 6 pages.
Final Office Action dated Sep. 17, 2018 in U.S. Appl. No. 14/875,800, 20 pages.
Notice of Allowance dated Sep. 24, 2018 in U.S. Appl. No. 15/873,158, 5 pages.
Notice of Allowance dated Sep. 24, 2018 in U.S. Appl. No. 15/837,856, 5 pages.
Non-Final Office Action received for U.S. Appl. No. 14/551,555, dated Oct. 10, 2018, 29 pages.

* cited by examiner

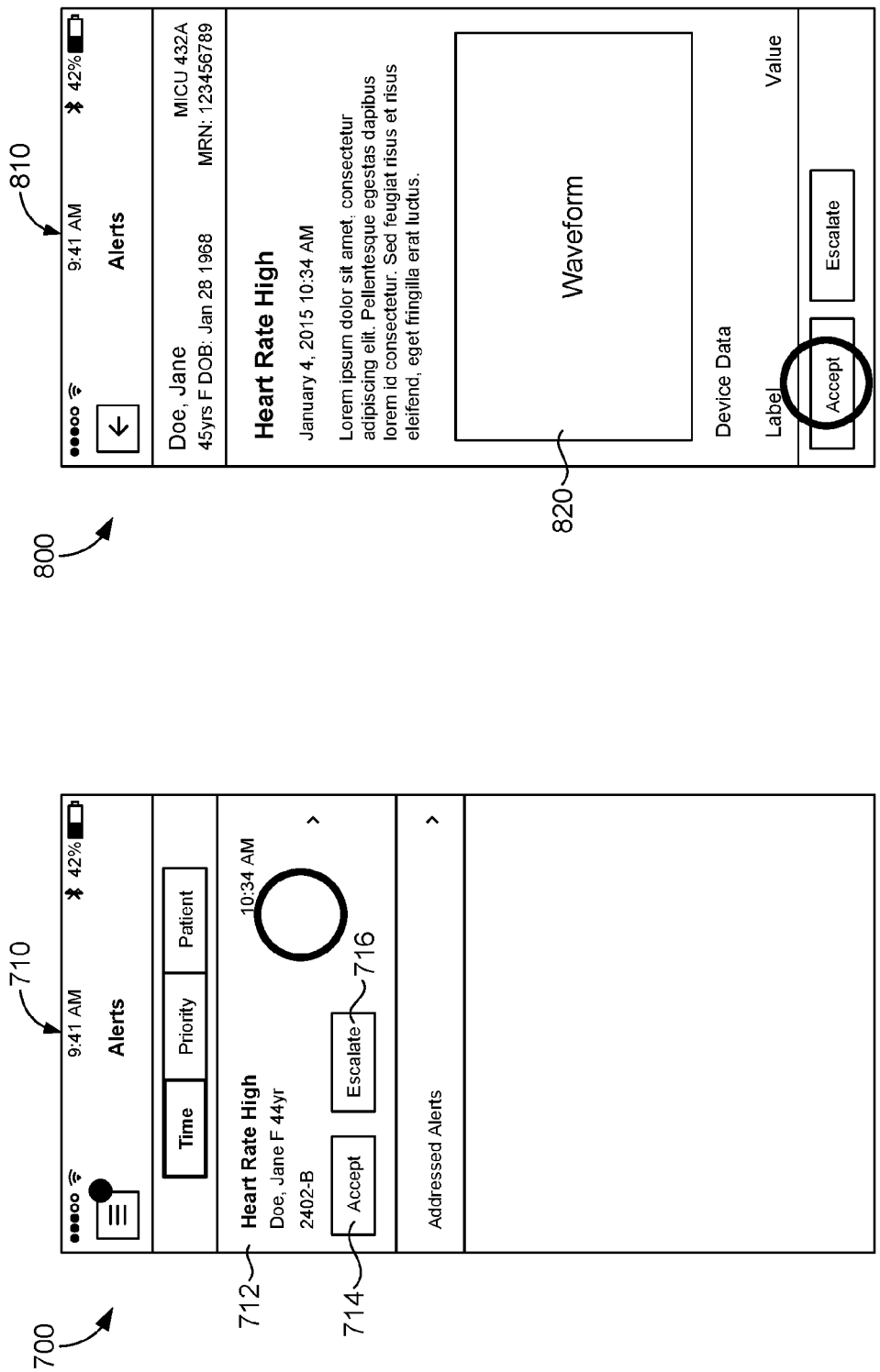

CLOSED LOOP ALERT MANAGEMENT

CROSS REFERENCE TO RELATED APPLICATIONS

This application is a continuation-in-part of U.S. patent application Ser. No. 14/877,808, filed on Oct. 7, 2015, and entitled "Alert Management Utilizing Mobile Devices," which is a continuation of U.S. patent application Ser. No. 13/731,191, filed on Dec. 31, 2012, and entitled "Alert Management Utilizing Mobile Devices," which issued as U.S. Pat. No. 9,185,202, on Nov. 10, 2015, the entireties of which are hereby incorporated by reference.

BACKGROUND

Typical nurse management of patient alerts utilizes stationary computer terminals located at, for example, a nursing station associated with a nursing unit. The stationary terminals are manned by unit secretaries who receive alerts or other important information related to patients on the unit. The unit secretary then identifies the clinicians assigned to those patients and may attempt to contact the clinicians through a variety of methods such as electronic paging, calling a patient's room to see if the clinician is in the room, or overhead paging. Clinicians then either have to call the unit secretary or return to the nursing station to retrieve the alerting information. The result is inefficient communication, unproductive workflows, and time lags between when alerting information is received and when it is acted on by the clinician.

In those situations where a patient alert is pushed to a clinician's mobile device, the alert often lacks important patient-contextual information, such as medical values, images, or device readings associated with the alert, that help the clinician in deciding how to appropriately respond to the alert. The clinician must then either return to the nursing station to access the information or open up a computer application on the mobile device to access the needed information—both of which consume valuable time resources. Further, a lack of visibility and coordination between clinicians receiving the same alert prevents clinicians from being aware of who is responding to an alert and what is happening at the alarm source.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-storage media for providing closed loop alert management. An alert related to a patient is communicated to a first tier via a messaging application. The first tier comprises one or more clinicians assigned to care for the patient. Upon receiving a response from a clinician in the first tier, an indication the clinician has responded to the alert is communicated to the first tier. Upon receiving no response from a clinician in the first tier, the alert may be communicated to other devices associated with the clinicians in the first tier or to a subsequent tier comprising one or more other clinicians.

BRIEF DESCRIPTION OF THE DRAWINGS

Embodiments are described in detail below with reference to the attached drawing figures, wherein:

FIGS. 5-8 are exemplary graphical user interfaces illustrating closed loop alert management in accordance with an embodiment of the present invention.

DETAILED DESCRIPTION

Figure 1:
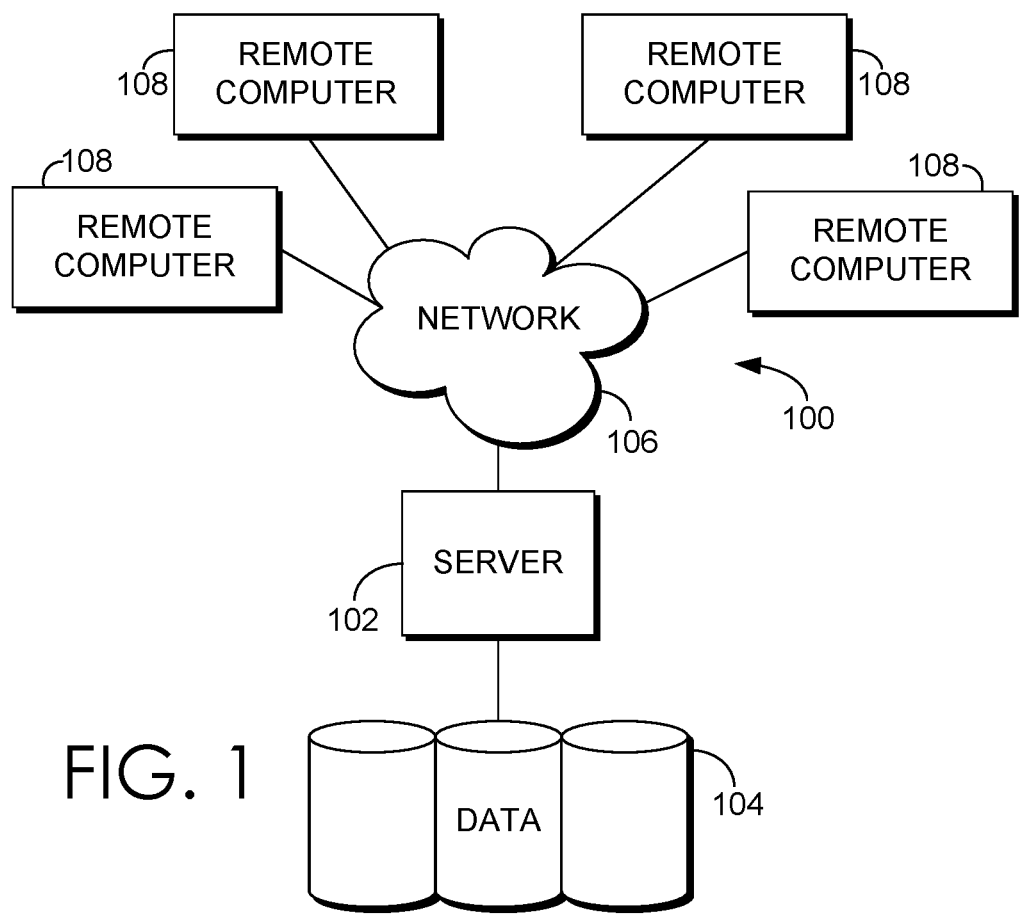
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As noted in the Background, typical nurse management of patient alerts utilizes stationary computer terminals located at, for example, a nursing station associated with a nursing unit. The stationary terminals are manned by unit secretaries who receive alerts or other important information related to patients on the unit. The unit secretary then identifies the clinicians assigned to those patients and may attempt to contact the clinicians through a variety of methods such as electronic paging, calling a patient's room to see if the clinician is in the room, or overhead paging. Clinicians then either have to call the unit secretary or return to the nursing station to retrieve the alerting information.

Further, a lack of visibility and coordination between clinicians receiving the same alert prevents clinicians from being aware of who is responding to an alert and what is happening at the alarm source. Additionally, in those situations where a patient alert is pushed to a clinician's mobile device, the alert often lacks important patient-contextual information, such as medical values, images, or device readings associated with the alert, that help the clinician in deciding how to appropriately respond to the alert. The clinician must then either return to the nursing station to access the information or open up a computer application on the mobile device to access the needed information—both of which consume valuable time resources.

Embodiments of the present invention are directed to providing closed loop alert management. An alert related to a patient is communicated to a first tier via a messaging application. The first tier comprises one or more clinicians assigned to care for the patient. Upon receiving a response from a clinician in the first tier, an indication the clinician has responded to the alert is communicated to the first tier. Upon receiving no response from a clinician in the first tier, the alert may be communicated to other devices associated with the clinicians in the first tier or to a subsequent tier comprising one or more other clinicians.

In embodiments, the information provides a link or anchor into a second application. The link or anchor may automate the login process for the second application so the clinician viewing the alert does not have to provide login credentials to access the second application. Further, the link or anchor may utilize the user, patient, or event context to bypass one or more screens within the second application so the second application opens to the item that triggered a review requirement or a task that needs to be completed by the viewing clinician. In this way, the inefficient communication, unproductive workflows, and time lags between when alerting information is received and when it is acted on by the clinician can be greatly reduced.

Additionally, resources of the device(s) being utilized by the clinician(s) may also be conserved (e.g., memory, processing time) because multiple applications are not required to be opened at all times, login events can be bypassed, context can be utilized to skip multiple screens and avoid user clicks/searches by automating this processing utilizing the links/anchors in the information. More simply, the information (i.e., user, patient, or event context) is passed through the alert so the appropriate application can be opened in the appropriate spot. In this way, the information drives other workflows and other computing devices are not needed to continue these workflows since they can be opened utilizing the messaging application.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs), wide area networks (WANs), and/or wireless LANs (WLANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
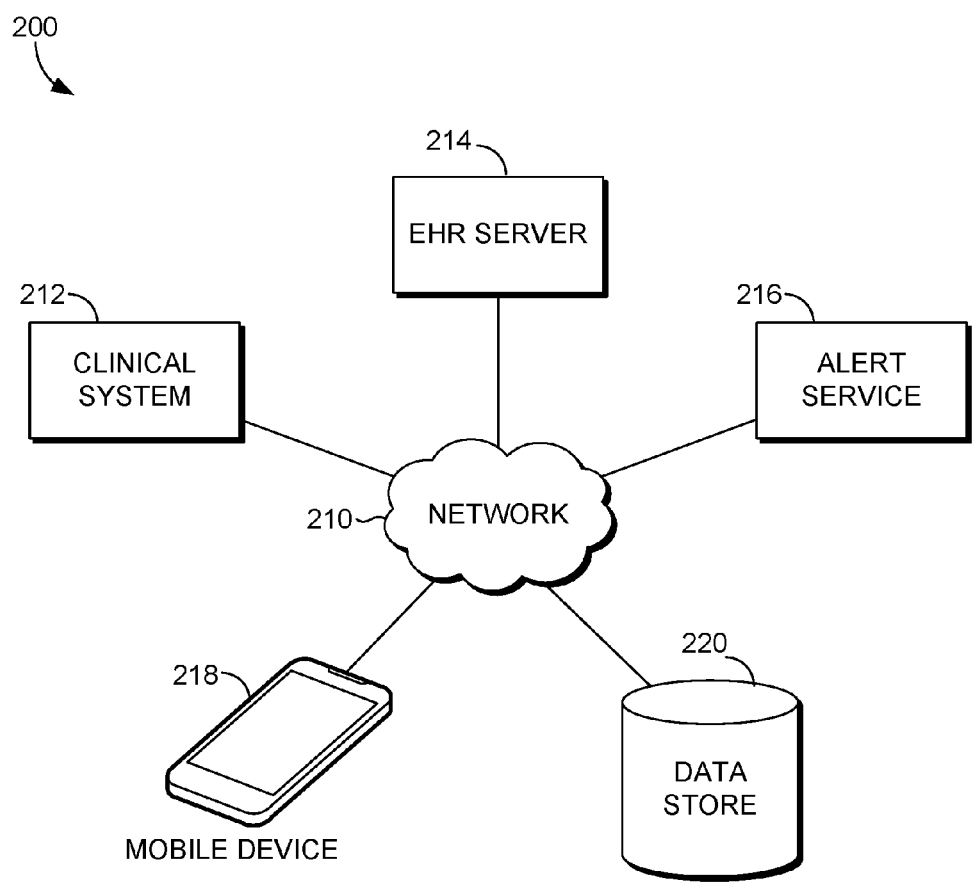
FIG. 2 is a block diagram of an exemplary system for providing closed loop alert management suitable to implement embodiments of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes a clinical system 212, an electronic health record (EHR) server 214, an alert service 216, a mobile device 218, and a datastore 220, all in communication with one another via a network 210. The network 210 may include, without limitation, one or more secure local area networks (LANs) or wide area networks (WANs). The network 210 may be a secure network associated with a facility such as a healthcare facility. The secure network 210 may require that a user log in and be authenticated in order to send and/or receive information over the network 216.

In some embodiments, one or more of the illustrated components/modules may be implemented as stand-alone applications. In other embodiments, one or more of the illustrated components/modules may be integrated directly into the operating system of the alert service 216. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the alert service 216 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 220 is configured to store information for use by, for example, the alert service 216, and/or the mobile device 218. The information stored in association with the data store 220 is configured to be searchable for one or more items of information stored in association therewith. The information stored in association with the data store 220 may comprise general information used by the alert service 216 and/or the mobile device 218. The information stored in association with the data store may be received from clinical system 212, which may include any number or type of medical devices that may be utilized to provide or measure patient care to a patient.

The data store 218 may store electronic health records (EHRs) of patients associated with one or more healthcare facilities. EHRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

Additionally, the data store 220 may store information concerning decision-support algorithms, reference materials, standards of care, recommendation protocols, alert protocols, and the like. This information may be specific to a healthcare facility, or the information may be promulgated by, for example, nationally-recognized medical organizations or governing bodies. Information stored in the data store 220 may also include staffing assignments (e.g., which clinicians are assigned to care for a patient), and availability information for the different clinicians. For instance, a clinician who is logged into the network 210 is flagged as available; a clinician who is logged into the network 210 but who has indicated that he/she is busy is flagged as available but busy; and a clinician who is not logged into the network 216 is flagged as offline. Staffing and availability information is continually updated. As used throughout this application, the term "clinician" generally means healthcare workers such as registered nurses, aids, respiratory therapists, physical therapists, occupational therapists, and the like. Clinicians such as these provide the day-to-day care of patients but normally do not have ordering privileges.

The content and volume of such information in the data store 220 are not intended to limit the scope of embodiments of the present invention in any way. Further, though illustrated as a single, independent component, the data store 220 may, in fact, be a plurality of storage devices, for instance, a database cluster, portions of which may reside on the alert service 216, the mobile device 218, and/or any combination thereof.

The mobile device 218 may be any type of wireless-telecommunications device. Such devices may include any type of mobile and portable devices including cellular telephones, personal digital assistants, tablet PCs, smart phones, and the like. The mobile device 218 includes a set of embodied computer-executable instructions that carry out various functional aspects of the invention. For example, the mobile device includes a messaging application. In one aspect, the mobile device 218 may be associated with or assigned to a clinician by the healthcare facility. In another aspect, the mobile device 218 may be owned by the clinician and registered with the healthcare facility. The mobile device 218 is capable of communicating with other associated or registered mobile devices by utilizing the secure network 210.

As shown, the mobile device 218 includes a display screen. The display screen is configured to display information to the user of the mobile device 218. The information may include communications initiated by and/or received by the mobile device 218, patient alerts, medical data related to the patient alerts, care lists, availability information, and the like. Embodiments are not intended to be limited to visual display but rather may also include audio presentation, combined audio/visual presentation, haptic feedback, and the like.

Components of the alert service 216 and the mobile device 218 may include a processing unit, internal system memory, and a suitable system bus for coupling various system components, including one or more data stores for storing information (e.g., files and metadata associated therewith). The alert service 216 and the mobile device 218 typically include, or have access to, a variety of computer-readable media.

The computing system environment 200 is merely exemplary. While the alert service 216 is illustrated as a single unit, it will be appreciated that the alert service 216 is scalable. For example, the alert service 216 may in actuality include a plurality of computing devices in communication with one another. Moreover, the data store 220, or portions thereof, may be included within, for instance, the EHR server 214, the alert service 216, and/or the mobile device 218 as a computer-storage medium. The single unit depictions are meant for clarity, not to limit the scope of embodiments in any form.

Alert service 216 is generally configured to receive information related to patient alerts. Such information may include data from medical devices electronically associated with a patient (i.e., from clinical system 212). Such devices are numerous but representative examples may include respirators, pulse oximeters, blood pressure monitors, blood glucose monitors, heart rate/rhythm monitors, input/output monitors, fetal monitors, and the like. Data from medical devices includes values, waveform tracings, images, and the like. Alert service 216 may also receive patient-identifying information from, for example, the data store 220 along with an alert history for the patient and normal value ranges for the patient.

Alert service may additionally receive staffing assignments from, for example, the data store 220 or a staffing/scheduling system associated with the healthcare facility caring for the patient. Staffing assignments include clinicians assigned to care for the patient during a specified time frame. Staffing assignments may depend on the patient's medical condition. By way of illustrative example, a patient who is rehabilitating from a serious car accident may be assigned a primary clinician (e.g., a nurse), a secondary clinician that cares for the patient when the primary clinician is busy, a respiratory therapist, a physical therapist, and an occupational therapist.

Alert service 216 is additionally configured to receive availability information for each of the patient's assigned clinicians. This information may be stored in association with the data store 220 or with the staffing/scheduling system. The availability status for any one clinician may include the status of available, available but busy, and offline. The status of available occurs when the clinician is logged in and authenticated to the secure network 210. The status of available but busy occurs when the clinician is logged in but has marked himself as busy using, for example, the mobile device 218. The status of offline occurs when the clinician is logged off of the network 210.

Location information for the clinicians, the patient, and devices associated with the patient may also be received by alert service 216 from, for example, a real-time location service associated with the healthcare facility. Such services use a variety of methods known in the art to track location information including radio-frequency identification (RFID) tags and sensors located throughout the healthcare facility. Login presence may also be received by alert service 216, for example, to determine if a clinician scheduled to work in a given location or with a given patient is logged into the system. If for example, that clinician is logged in but set their presence to "on break", alert service 216 might bypass that clinician.

Alert service 216 additionally receives information from the nurse call system of the healthcare facility. The nurse call system enables communication between the patient and clinicians utilizing a number of different devices such as a pillow speaker. Some systems enable the patient to enter information concerning the nurse call before it is transmitted to the nurse. For instance, the patient may input that he/she would like ice chips, or that he/she is having difficulty breathing or is in pain.

Alert service 216 may utilize the information in association with clinical guidelines, alerting protocols, and/or standardized recommendations to determine if and what type of alert should be generated. The alerts can be broadly categorized as critical alerts and non-critical alerts. Critical alerts can be generally defined as those alerts that can have a negative impact on a patient's health if not addressed in a timely manner. On the other hand, non-critical alerts can be generally defined as those alerts that do not negatively impact the patient's health if not addressed in a timely manner. Some representative examples of critical alerts may include Asystole (i.e., heart has stopped), heart arrhythmia, presence of sepsis indicators, and the like. Some representative examples of non-critical alerts include patient requests for ice chips or toiletry assistance, lab values or device readings that are slightly outside of the normal range, indication that a new patient order has been received, and the like.

Alert service 216 is configured to communicate patient alerting information to the mobile device 218. The alerting information includes an alert identifier, status indicators related to the alert, patient-identifying information, location corresponding to the alert, lab values related to the alert, EHR information related to the alert, medication orders related to the alert, and device readings related to the alert. In one aspect, lab values, medication orders, and device readings (e.g., waveform tracings, values, and/or images) are related to the alert if they triggered the alert. The waveform tracings, values, and/or images may be time-stamped and may include a predefined time period before the alert was triggered, a time period corresponding to the alert trigger, as well as a predefined time period after the alert was triggered. The mobile device 218 then presents this information to the clinician as more fully described below.

In one aspect, the patient's alerting information is initially communicated to the mobile devices associated with the patient's care team (e.g., the first tier). If a clinician in the first tier rejects the alert, the alert service 216 may communicate the rejection to other clinician in the first tier. If each clinician in the first tier rejects the alert, the alert service 216 may communicate the patient's alerting information to the subsequent tier. If the subsequent tier rejects the alert, the alert service 216 may communicate the alert to mobile devices associated with every available member of the patient's care team.

In another aspect, the alert service 216 determines the clinician role best suited to initially address the particular patient alert, and communicates the alerting information to mobile device(s) associated with clinicians (e.g. the first tier) in that role. By way of illustrative example, a patient alert indicates that a patient's oxygen saturation levels have dropped below recommended ranges. The alert service 216 determines that a respiratory therapist would be suited to address this alert and communicates the alerting information to the mobile device(s) associated with available respiratory therapist(s). The alerting information may at the same time be communicated to the mobile device(s) associated with the patient's care team.

In yet another aspect, the alert service 216 determines clinicians in close proximity to the patient that is the subject of the alert, determines if the role of those clinicians that are located close to the patient is suited to meet the particular patient alert, and, if so, communicates the initial alert to those clinicians (e.g., first tier). The alerting information may at the same time be communicated to the mobile device(s) associated with other clinicians in the patient's care team. Any and all of such aspects, and any combination thereof, are contemplated as being within the scope of the invention.

The alert service 216 is further configured to receive communications from the mobile device(s) 218. Such communications may comprise notifications that the alert has been acknowledged and accepted by a recipient so that other recipients may be notified of the acknowledgment and acceptance. This information is time-stamped and may be stored in association with the patient's EHR. Another communication may comprise a notification that the alert was rejected by a recipient so other recipients are aware that the alert still needs to be acknowledged and accepted. Other communications from the mobile device may include indicators that a recipient of the alert has communicated the alert to other members of the care team. The indicators may include the identities of the additional recipients, whether the additional recipients acknowledged receipt of the alert, and a time the alert was forwarded. Communications from the mobile device(s) 218 may additionally include requests for more information.

As described above, the mobile device(s) 218 includes a messaging application. The messaging application is generally configured to receive communications, such as from the alert service 216 or from other mobile devices. For example, the alert service 216 communicates an alert related to a patient, via the messaging application, to mobile device(s) 218. The mobile device(s) may be associated with clinicians in a first tier assigned to care for the patient The messaging application may enable the mobile device(s) 218 to respond to the alert (e.g., accepting, rejecting, forwarding, forwarding with response options, etc.). These responses may be communicated to the alert service 216, and as described below, to other clinicians receiving the alert. Further, the ability to reject or forward the alert may be limited based on availability of other clinicians. Similarly, alert service 216 may bypass the clinician that would normally receive the alert if it is determined that clinician is unavailable (e.g., the clinician is on break or with another patient). Based on one or more responses received from mobile device(s) 218, information may be communicated by alert service 216 to a different clinician device (e.g., a workstation, tablet, or different mobile device) if, for example, the clinician is in a different location than the mobile device or the clinician is currently utilizing a different device. Information may also be communicated by alert service 216 to another clinician.

Additionally, the messaging application communicates back to the alert service 216 when an alert has been responded to by a clinician in the first tier. For example, if clinician A and clinician B are both in the first tier, both clinicians get the same alert. Assuming clinician B responds, clinician A needs visibility to that response and alert service 216 communicates to clinician A that clinician B has responded. If clinician B accepts, then clinician A is made aware by alert service 216 so clinician A does not need to respond or follow up to the same alert. On the other hand, if clinician B rejects the alert, then alert service 216 communicates to clinician A needs that a response may still be needed. Similarly, if clinician B does not respond on a mobile device, but goes to the room and silences or resolves the alarm anyway that has triggered the alert, then clinician A is notified by alert service 216 when the device is silenced or stops alarming so clinician A does not need to respond or follow up. As can be appreciated, when a response occurs or the alarm is silenced or resolved, such response, silence, or resolution is communicated to all members of the current tier and/or any members of the current tier and previously notified tiers.

As used herein, the information may include user, patient, or event context corresponding to the alert. If the alert is forwarded to another clinician or the subsequent tier, the clinician forwarding the alert may select options that limit response options for the receiving clinician or the subsequent tier. For example, the receiving clinician may be allowed to accept or reject the alert only, and not forward the alert to a third clinician.

The information may include data received from one or more medical devices associated with the patient, one or more lab values for the patient, or medication orders for the patient (such as may be received and provided by clinical system 212). The data may be communicated from the one or more medical devices associated with the patient as patient context in the alert. Based on the data from the one or more medical devices associated with the patient, the one or more lab values for the patient, or the medication orders for the patient, the alert may be escalated or suppressed.

Based on the information, context may be passed by the messaging application to switch to a second application. For example, alert service 216 may identify that some of the patient or event context corresponds to data that may be more easily reviewed within a native application (e.g., waveform tracings), such as one that may be provided by clinical system 212. Similarly, the alert may require the clinician to perform some action within the native application. Accordingly, the alert service 216 may communicate, via the messaging application, a link or anchor into the native application in association with the alert.

The link or anchor automates the login process for the second application so the first clinician or the second clinician does not have to provide login credentials. Additionally, the link or anchor utilizes the user, patient, or event context to bypass one or more screens within the second application so the second application opens to the appropriate point in the workflow. In other words, the link or ancho enables the second application to open to the item that triggered a review requirement or a task that needs to be completed by the first clinician or the second clinician (i.e., prompted the alert).

Additionally, messaging application enables conversations threads between clinicians in the first and/or subsequent tiers. The conversation threads are associated with and may include information from the alert (including links or anchors into the second application). Further, these conversation threads may be stored in the EHR.

Figure 3:
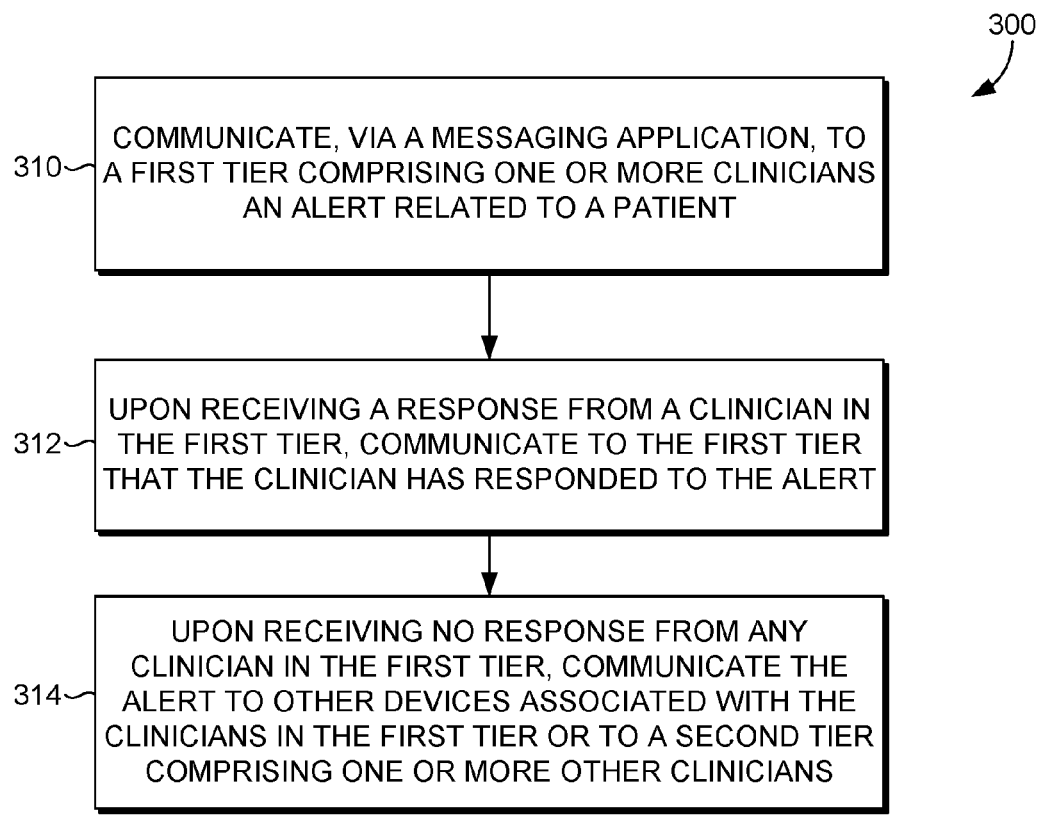
FIG. 3 is a flow diagram of an exemplary method of providing closed loop alert management in accordance with an embodiment of the present invention.

Turning now to FIG. 3, a flow diagram is depicted of an exemplary method 300 of providing closed loop alert management, in accordance with an embodiment of the present disclosure. For instance, the method 300 may be employed utilizing the alert system 200 of FIG. 2. As show at step 310, an alert related to a patient is communicated, via a messaging application, to the first tier comprising one or more clinicians. The receipt of the alert may be accompanied by an auditory sound or a physical action such as a vibration to alert the clinician that an alert has been received.

If the alert is a critical alert, the alert may be configured to interrupt or supersede any applications that are currently running on the device. For instance, the alert may be presented as a pop-up that overlies other content on the device. The clinician may be unable to access other functionalities associated with the device until the clinician acknowledges the alert by either accepting or rejecting the alert. This helps to ensure that critical alerts are addressed in a timely manner by the clinician.

In embodiments, the alert includes patient-identifying information such as the patient's name, room location, and the patient's date of birth. The alert also includes an alert identifier and an alert status. The alert identifier conveys to the clinician the nature of the alert. For instance, identifiers may include phrases such as "ADE" for an adverse drug event, "HR high" to indicate the heart rate is outside of the normal range, "Low SPO2" to indicate low blood oxygen saturation, "Diastolic High" to indicate that diastolic blood pressure is high, and "SEPSIS: SIRS Criteria Met" to indicate that the patient is possibly becoming septic. These are just a few representative examples provided for illustration purposes only. Any identifier that provides a brief description of the nature of the alert is contemplated as being within the scope of the invention. The alert status may be indicated by textual phrases such as "Critical Alert," color coding, flashing images, and the like.

Upon receiving a response from a clinician in the first tier, an indication that the clinician has responded is communicated, at step 312, to the first tier. The alert may include user, patient, or event context. In embodiments, the responses may include the one or more responses include accepting the alert, rejecting the alert, forwarding the alert, or forwarding the alert with second clinician response options.

The second clinician response options may be inherited from response options provided to the first clinician via the alert. Alternatively, the second clinician response options may be selected by the clinician forwarding the alert. For example, the clinician may wish to limit the second clinician to accepting or rejecting the alert only, and upon selecting such options prior to forwarding the alert, the second clinician is only able to accept or reject the alert (and unable to forward the alert to a third clinician).

Additionally or alternatively, the alert may provide a link or anchor into the second application. In embodiments, the link or anchor automates the login process for the second application so the first clinician or the second clinician does not have to provide login credentials. For example, the link or anchor may utilize the user, patient, or event context to bypass one or more screens within the second application so the second application opens to the appropriate point in the workflow. The appropriate point in the workflow for the second application may be the item that triggered a review requirement or a task that needs to be completed by the first clinician or the second clinician. The second application may be opened by the messaging application when the clinician selects the link or anchor provided by the alert.

Upon receiving no response from any clinician in the first tier, the alert is communicated, at step 314, to other devices associated with the clinicians in the first tier or to a subsequent tier comprising one or more other clinicians. In some embodiments, upon receiving a rejection of the alert from a clinician in the first tier, automatically communicating, based on clinician availability, the alert to another clinician in the first tier or to a subsequent tier. Clinician availability may be determined from a scheduling system, a staffing assignment system, or a location detecting system. For instance, if the clinician rejects the alert, is already with another patient or otherwise unavailable, the alert may be automatically communicated to another clinician or to a subsequent tier.

In embodiments, upon receiving a response from a clinician to forward the alert, a list of one or more additional clinicians assigned to the patient may be presented on the first mobile device. The list may include the names of the other clinicians, a thumbnail picture of the clinician, roles associated with each of the clinicians, locations of the clinicians, and/or the availability status of the clinicians. The list may be ordered based on clinician role such that clinicians most suited to meet the alert needs are presented at the top of the list. The list may also be ordered based on proximity to the patient location. Thus the clinician of the alert can quickly assess which clinicians are located closest to the patient. The list may additionally be ordered based on a combination of user role and proximity to the patient. Other ways of ordering the list include alphabetical order and availability status. Any and all such aspects, and any combination thereof, are contemplated as being within the scope of the invention.

Clinicians on the list may be associated with an availability status indicator. These indicators may indicate that the clinician is available, available but busy, or is not currently logged into the network. Availability status indicators may include color-coded indicators such as green for available, white for offline, and red for available but busy. Other ways of indicating availability status may include textual descriptions, and other types of visual indicators known in the art.

In some embodiments, the clinician receiving the alert may elect to call a clinician on the list. In another aspect, the alert is communicated as short message service-like or multimedia message service-like messaging patterns and protocols. The alert that is communicated to the selected clinician may include patient-identifying information, the alert identifier, the alert status, lab values, device readings, medication orders, images, waveforms, and/or trending graphs associated with the alert (which may be derived from links or anchors into a second application as described above). Further, when the alert is communicated as short message service-like or multimedia message service-like messaging patterns and protocols, the original recipient may optionally enter a textual message in association with the alert. In one aspect, the original recipient receives a notification when the selected clinician acknowledges the alert.

In some embodiments, data is received from one or more medical devices associated with the patient, one or more lab values for the patient, nurse call requests, or medication orders for the patient. The data may be communicated from the one or more medical devices associated with the patient as patient context in the alert. Based on the data from the one or more medical devices associated with the patient, the one or more lab values for the patient, the nurse call requests, or the medication orders for the patient, the alert may be escalated or suppressed.

In some embodiments, based on a state of the clinician device, a criticality of the alert, or the tier the alert is communicated to (e.g., second or third tier), the presentation of the alert may be changed. For example, tones, durations, patterns, haptic, audio, or visual characteristics of the alert may be changed to indicate a higher or lower criticality of the alert. In another example, tones durations, patterns, haptic, audio, or visual characteristics of the alert may be changed if the clinician device is detected in proximity to the patient (or device) associated with the alert (e.g., if the clinician device is detected next to the device that is causing the alert, it can be assumed the clinician is also in proximity and the alert may be presented in a less critical manner since the clinician is likely already aware). If the alert has been communicated to multiple tiers without a response, the tones, durations, patterns, haptic, audio, or visual characteristics of the alert may be changed to indicate an increased urgency.

In some embodiments, conversation threads are enabled between clinicians. The conversation threads may be associated with and/or include information from the alert. Further, conversation threads may be enabled between other members of a care team for the patient (or other tiers). These conversation threads may also be associated with and/or include information from the alert. The conversation threads between members of a care team for the patient may be stored in an EHR, where they may also be associated with and/or information from the alert.

Figure 4:
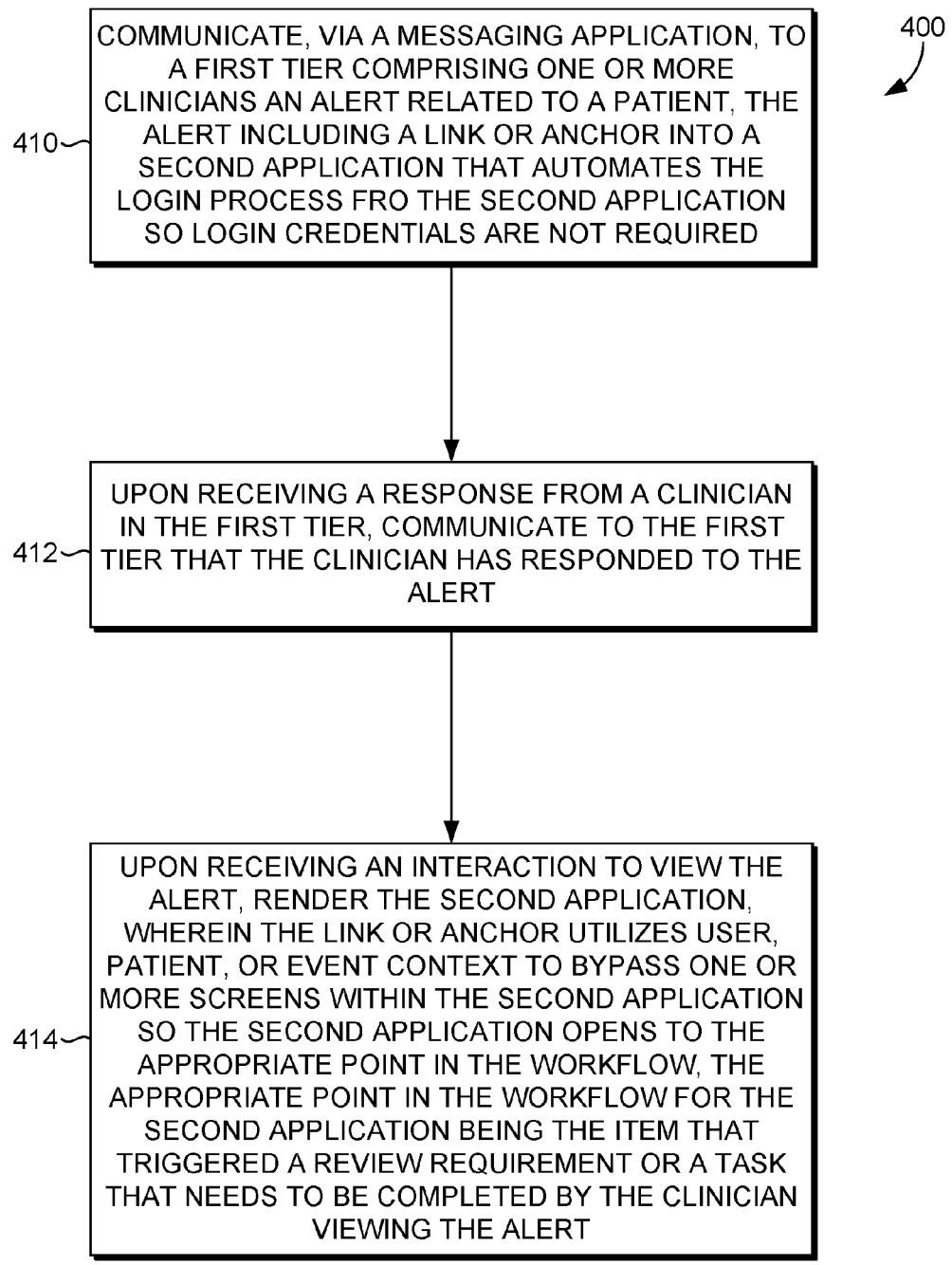
FIG. 4 is a flow diagram of an exemplary method of providing closed loop alert management in accordance with an embodiment of the present invention.

Turning now to FIG. 4, a flow diagram is depicted illustrating an exemplary method 400 of providing closed loop alert management, in accordance with an embodiment of the present disclosure. For instance, the method 400 may be employed utilizing the alert system 200 of FIG. 2. As show at step 410, an alert related to a patient is communicated, via a messaging application, to a first tier comprising one or more clinicians an alert related to a patient. The alert may include a link or anchor into a second application that automates the login process for the second application so login credentials are not required.

Upon receiving a response from a clinician in the first tier, an indication the clinician has responded is communicated, at step 412, to the first tier that the clinician has responded the alert (or, to all members of the current notification tier and/or any members of the current tier and previously notified tiers). Upon receiving an interaction to view the alert, at step 414, the second application is rendered. The link or anchor utilizes user, patient, or event context to bypass one or more screens within the second application so the second application opens to the appropriate point in the workflow. For clarity, the appropriate point in the workflow for the second application is the item that triggered a review requirement or a task that needs to be completed by the clinician viewing the alert.

In one embodiment, failure by the first tier to address the alert within a predetermined period of time causes the alert to be automatically communicated to additional devices associated with clinicians in the first tier or to a subsequent tier comprising other clinicians. The predetermined period of time may range from one minute up to five minutes and may be dependent on the criticality of the alert.

Figure 5:
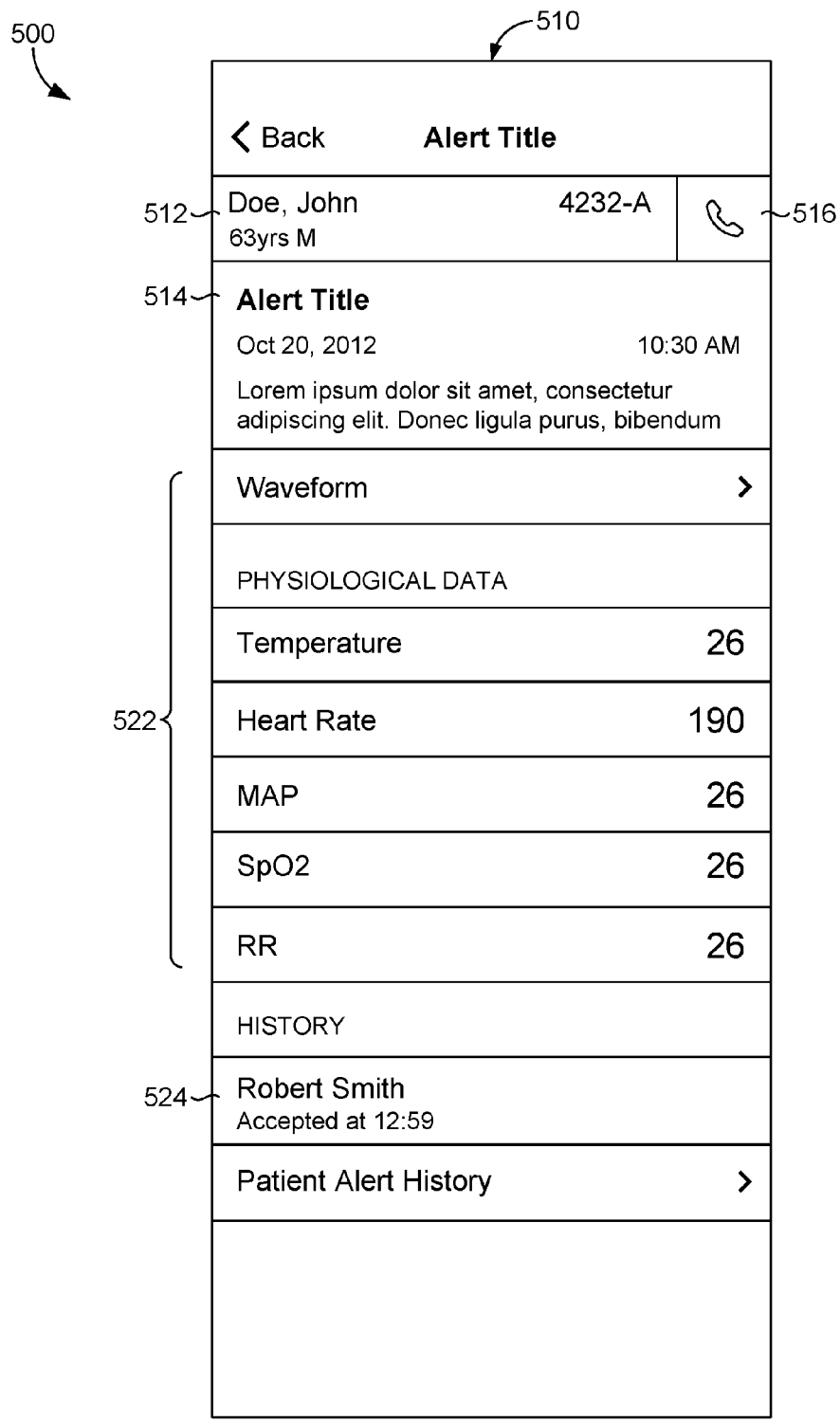

Turning now to FIG. 5, graphical user interface 500 illustrates closed loop alert management using a mobile device such as the mobile device 220 of FIG. 2. GUI 500 depicts an alert 510 presented on the mobile device. The alert 510 includes a patient identification area 512 that presents information such as patient name, patient identification number, room number, date of birth, age, sex, and the like. The alert 510 may also include an alert identifier 514. The alert may have a call option 516. When the call option 516 is selected, the recipient is automatically presented with a call contact list comprising members of the patient care team. The call contact list includes names of the clinicians, pictures of the clinicians, availability indicators, location information, user role, and the like. In another aspect, when the call option 516 is selected, a call to the patient room is automatically placed so that the clinician can speak with the patient.

Additional information 522 is presented that may include such items as medications, lab values, device readings, and the like. Medication information may include the dosage amount, the dosage route, and the day and time when the medication was last administered. Lab value information and device reading information may include a normal range, a previous value, a current value, a date and time when obtained, and an indicator that indicates whether the current value is greater or lesser than the previous value. Each of the items of information 522 provides patient context to the alert 510 and assist the alert recipient to make an informed decision regarding how to effectively address the alert. An acceptance area 524 indicates the time the alert 510 was accepted by the recipient. Each item of additional information 522 may include a link or anchor into a second application. If the clinician selects a link or anchor, the second application may be rendered with the messaging application.

Figure 6:
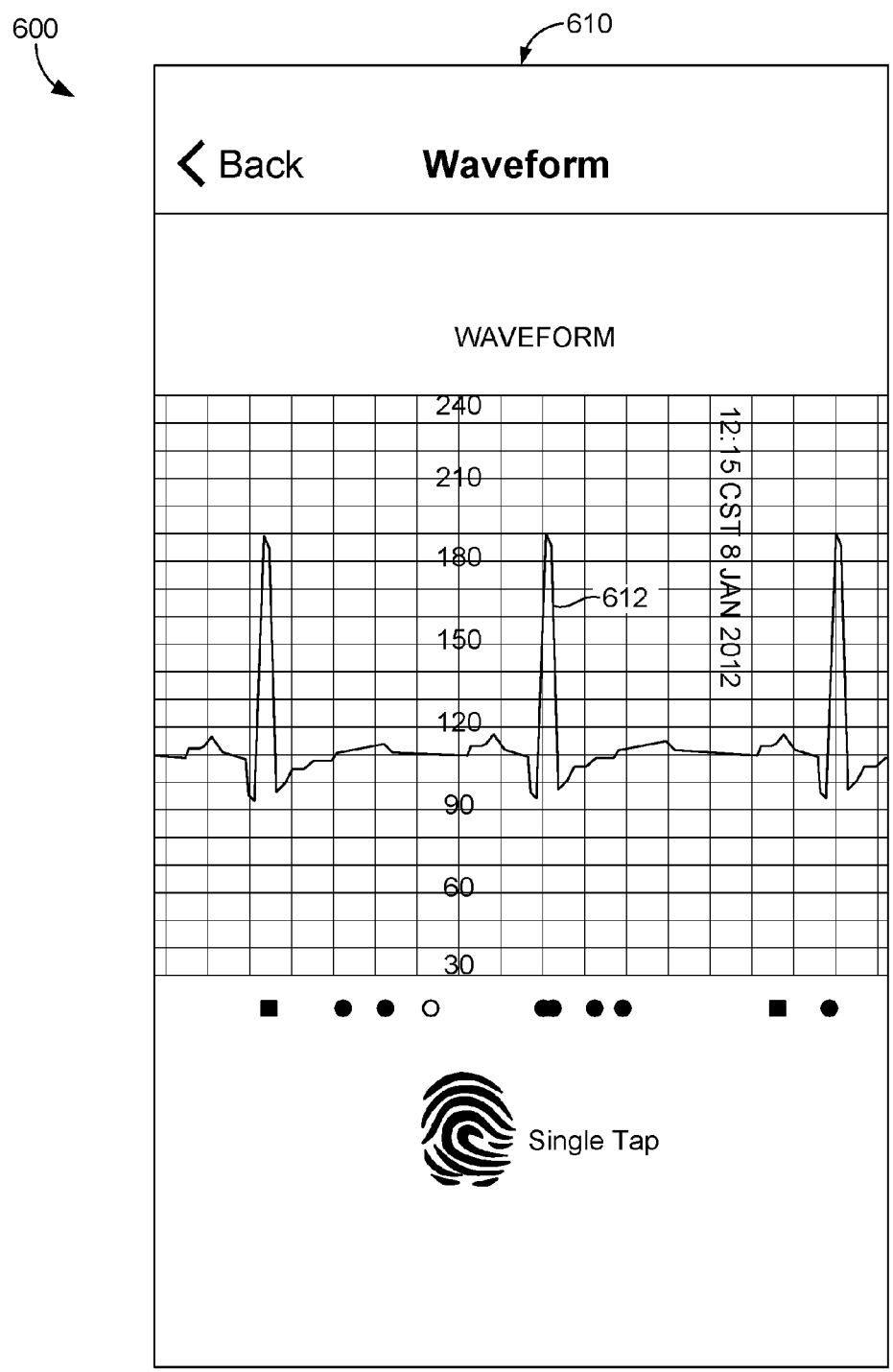

In FIG. 6, graphical user interface 600 illustrates closed loop alert management using a mobile device such as the mobile device 220 of FIG. 2. GUI 600 depicts a second application 610 rendered within the messaging application on the mobile device. As illustrated, the second application 610 provides the waveform tracing. The waveform tracing 612 is captured and time-stamped by the patient's device at the time the alert was triggered and may include segments of time before and after the alert was triggered to provide additional context for the waveform tracing 612. Although a waveform tracing 612 is shown, it is also contemplated that an image captured by a camera or a monitoring device may be presented. For instance, a clinician may take a picture of a patient's wound and this image may be included with the alert 610. The waveform tracing 612, and/or image, is used by the alert recipient to select other clinicians to notify so that the alert can be properly addressed.

Turning now to FIG. 7, graphical user interface 700 illustrates closed loop alert management using a mobile device such as the mobile device 220 of FIG. 2. GUI 700 depicts an alert 710 that has not yet been accepted by a clinician. The alert 710 includes an alert identifier 712, an accept option 714, and an escalate option 716. If the clinician chooses to accept the alert 710 by tapping, swiping, or otherwise selecting, a second application may be rendered within the messaging application (if a link or anchor is associated with the alert).

FIG. 8 depicts graphical user interface 800 illustrating the second application being rendered within the messaging application providing the alert 810. As illustrated, the second application 820 provides a waveform tracing. The waveform tracing may be captured and time-stamped by the patient's device at the time the alert was triggered and may include segments of time before and after the alert was triggered to provide additional context for the waveform tracing. Although the second application 820 is illustrated as providing a waveform, it is also contemplated that an image captured by a camera or a monitoring device may be presented. For instance, a clinician may take a picture of a patient's wound and this image may be included with the alert 810. The waveform tracing, and/or image, is used by the alert recipient to select other clinicians to notify so that the alert can be properly addressed.

As can be understood, embodiments of the present disclosure provide for an objective approach for providing closed loop alert management. The present disclosure has been described in relation to particular embodiments, which are intended in all respects to be illustrative rather than restrictive. Alternative embodiments will become apparent to those of ordinary skill in the art to which the present disclosure pertains without departing from its scope.

From the foregoing, it will be seen that this disclosure is one well adapted to attain all the ends and objects set forth above, together with other advantages which are obvious and inherent to the system and method. It will be understood that certain features and subcombinations are of utility and may be employed without reference to other features and subcombinations. This is contemplated by and is within the scope of the claims.

What is claimed is:

1. One or more non-transitory computer-storage media storing computer-useable instructions that, when used by one or more processors, cause the one or more processors to perform operations comprising:
    communicating, via a messaging application, to a first tier comprising one or more clinicians an alert related to a patient;
    upon receiving a response from a clinician in the first tier, communicating to the first tier that the clinician has responded the alert; and
    upon the response being a rejection of the alert from the clinician, automatically communicating, based on clinician availability, the alert to another clinician in the first tier or a subsequent tier.

2. The media of claim 1, further comprising communicating information corresponding to the alert to the first tier, the information including user, patient, or event context.

3. The media of claim 1, wherein clinician availability is determined from a scheduling system, a staffing assignment system, a login presence, or a location detecting system.

4. The media of claim 1, wherein the response includes accepting the alert, rejecting the alert, forwarding the alert, or forwarding the alert with second clinician response options.

5. The media of claim 2, wherein the information further includes a link or anchor into a second application.

6. The media of claim 5, wherein the link or anchor automating the login process for the second application so the clinician in the first tier does not have to provide login credentials for the second application.

7. The media of claim 6, wherein the link or anchor utilizes the user, patient, or event context to bypass one or more screens within the second application so the second application opens to the appropriate point in the workflow.

8. The media of claim 7, wherein the appropriate point in the workflow for the second application is the item that triggered a review requirement or a task that needs to be completed by the clinician in the first tier or the subsequent tier.

9. The media of claim 1, further comprising receiving data from one or more medical devices associated with the patient, one or more lab values for the patient, nurse call requests, or medication orders for the patient.

10. The media of claim 9, communicating the data form the one or more medical devices associated with the patient as patient context in the alert.

11. The media of claim 9, further comprising, based on the data from the one or more medical devices associated with the patient, the one or more lab values for the patient, or the medication orders for the patient, escalating the alert or suppressing the alert.

12. The media of claim 1, further comprising based on a state of a clinician device or a criticality of the alert, changing the presentation of the alert.

13. The media of claim 12, wherein changing the presentation of the alert includes changing the tones, durations, patterns, haptic, audio, or visual characteristics of the alert.

14. The media of claim 4, wherein the second clinician response options are inherited from response options provided to the first tier via the alert.

15. The media of claim 4, wherein the second clinician response options are selected by the clinician in the first tier forwarding the alert or are alternate response options based on the alert having been escalated.

16. The media of claim 1, further comprising enabling conversation threads between clinicians in the first tier or between clinicians in the first tier and the subsequent tier, wherein the conversation threads are associated with information from the alert.

17. The media of claim 1, further comprising storing conversation threads in an electronic health record, wherein the conversation threads are associated with information from the alert.

18. A computer-implemented method comprising:
    communicating, via a messaging application, to a first tier comprising one or more clinicians an alert related to a patient, the alert including a link or anchor into a second application that automates the login process for the second application so login credentials are not required;

upon receiving a response from a clinician in the first tier, communicating to the first tier that the clinician has responded the alert; and upon receiving a selection of the link or anchor, opening the second application, wherein the link or anchor utilizes user, patient, or event context to bypass one or more screens within the second application so the second application opens to the appropriate point in the workflow, the appropriate point in the workflow for the second application being the item that triggered a review requirement or a task that needs to be completed by the clinician viewing the alert.

19. A system in a healthcare computing environment comprising:

a processor; and a non-transitory computer storage medium storing computer-useable instructions that, when used by the processor, causes the processor to:

communicate, via a messaging application, to a first tier comprising one or more clinicians an alert related to a patient; and upon receiving a response from a clinician in the first tier, communicate to the first tier that the clinician has responded the alert, the response forwarding the alert to a second clinician with second clinician response options that are inherited from response options provided to the first tier via the alert.

* * * * *